(12) United States Patent
Greelish

(10) Patent No.: US 7,076,992 B2
(45) Date of Patent: Jul. 18, 2006

(54) METHOD AND APPARATUS FOR CALIBRATING POSITION AND THICKNESS IN ACOUSTIC HULL TESTING

(76) Inventor: Stephen John Greelish, 130 Pond Cir., Mashpee, MA (US) 02649

( * ) Notice: Subject to any disclaimer, the term of this patent is extended or adjusted under 35 U.S.C. 154(b) by 0 days.

(21) Appl. No.: 10/981,835

(22) Filed: Nov. 5, 2004

(65) Prior Publication Data

US 2005/0092091 A1   May 5, 2005

Related U.S. Application Data

(60) Provisional application No. 60/517,950, filed on Nov. 6, 2003.

(51) Int. Cl.
  *G01N 29/30* (2006.01)
  *G01V 13/00* (2006.01)
(52) U.S. Cl. ..................... 73/1.86
(58) Field of Classification Search ............ 73/1.82, 73/1.86
See application file for complete search history.

(56) References Cited

U.S. PATENT DOCUMENTS

| | | | | |
|---|---|---|---|---|
| 3,733,889 A | * | 5/1973 | Proctor, Jr. | 73/629 |
| 3,958,451 A | * | 5/1976 | Richardson | 73/644 |
| 5,029,476 A | * | 7/1991 | Metala et al. | 73/620 |
| 5,163,047 A | * | 11/1992 | Perdikaris et al. | 370/401 |
| 5,167,910 A | * | 12/1992 | Omote et al. | 376/434 |
| 5,837,880 A | * | 11/1998 | Shakinovsky et al. | 73/1.86 |
| 5,909,176 A | * | 6/1999 | Schrott et al. | 340/572.1 |
| 6,125,704 A | * | 10/2000 | Wang | 73/602 |
| 6,131,659 A | * | 10/2000 | Johnson | 166/250.05 |

FOREIGN PATENT DOCUMENTS

DE   3538711 A1 *  4/1987
JP   04313096 A   * 11/1992

* cited by examiner

*Primary Examiner*—Hezron Williams
*Assistant Examiner*—Rose M. Miller
(74) *Attorney, Agent, or Firm*—Robert K. Tendler

(57) ABSTRACT

A system is provided for calibrating an acoustic hull integrity sensing system by providing a coupon attached to the interior surface of the hull, in which the coupon has a stepped calibration block, with one of the steps approximating the thickness of the hull to be measured at the position of the coupon. The stepped calibration block is made of a material with the same acoustic properties as that of the hull. Acoustic energy is propagated towards the hull and passes through the hull, the interface between the hull and the block and to the interface between the stepped surface and the surrounding material, with reflected acoustic energy having a time of arrival at a sensor measured through the use of zero crossing detectors, in which the thickness of the stepped block that most closely approximates that of the hull is multiplied by a ratio that is the time for energy to propagate through the hull, divided by the time for the energy to propagate through the stepped block.

18 Claims, 8 Drawing Sheets

METHOD AND APPARATUS FOR CALIBRATING POSITION AND THICKNESS IN ACOUSTIC HULL TESTING

RELATED APPLICATIONS

This Application claims rights under 35 USC § 119(e) from Provisional U.S. application Ser. No. 60/517,950 filed Nov. 6, 2003, the contents of which are incorporated herein by reference.

FIELD OF THE INVENTION

This invention relates to hull surveying and more particularly to a system for calibrating acoustic-based hull integrity sensing systems.

BACKGROUND OF THE INVENTION

As described in co-pending patent application Ser. No. 10/935,986 filed Sep. 8, 2004 by Steven Greelish entitled "Method and Apparatus For Performing an Ultrasonic Survey," incorporated herein by reference, a system is provided for surveying a ship's hull by accurately ascertaining the position of the ship's hull relative to, for instance, a robotic sensor flying around the hull. In this system a coordinate system is established so that the position of the robot relative to the hull can be ascertained, thus to permit acoustic hull measurements.

In hull inspections, the purpose is to determine erosion or wasting of the hull so as to be able to certify the seaworthiness of the ship. Determining seaworthiness depends upon accurate measurements of the thickness of the hull, and even hull plating and coatings or paint, with coating thickness usually measured in thousandths of an inch. In order for the ship to be certified as seaworthy, classification societies use hull thickness information to determine the seaworthiness of a ship. However, these societies require a certain level of calibration that ensures that the measurements obtained are accurate.

In the past, in order to convince classification societies of the accuracy of the measurements, it has been the practice to obtain a sample of the ship's hull and to calibrate the instruments either away from the ship, or to send a diver down with a test plate for the calibration process.

While high accuracy thickness measurements can be made using high quality, high frequency instruments, it is a requirement for these instruments that the sensor be attached to the hull. This is impractical for in-water surveying systems and thus a lower frequency system is required so that the acoustic energy can penetrate the water column and then the hull. However, lower frequency systems result in degraded performance.

Moreover, using test samples that are transported to the test location at the hull results in a calibration system that suffers from changes in temperature, instrument damage and calibration shifts as one transports the test sample and/or instrument from one site to the other. Moreover, as mentioned above the thickness measurements can suffer degradation in terms of the frequency that is used, with the lower frequencies providing less accurate results.

There is another problem with the way in which acoustic thickness measuring instruments are calibrated and that is that the measurements themselves generally measure the timing of the receipt of a reflected pulse by integrating the return signal and measuring the position of the resulting signal envelope. These integrating systems suffer from the fact that they are amplitude-dependent, meaning that the timing of the return pulse as measured by the envelope shifts depending on the amplitude of the returned signal. Thus, any system that uses integration, or rectification and integration, suffers from the fact that the actual measurement is affected by the amplitude of the signal.

The result is that, for some of these hull-measuring systems, the thickness measurement may be off by 10 or 15%.

There is thus a requirement to be able to measure the hull thickness to within one-half of one percent, which translates in some cases to measurement accuracy better than one one-thousandth of an inch.

Also, a problem exists as to where exactly on the ship's hull the measurement is made. Locating the precise position on the hull is oftentimes difficult for divers, since they are oftentimes in brackish or clouded water adjacent to the hull. Therefore, there is a requirement to be able to identify exactly where on the hull the thickness measurement is being made.

SUMMARY OF INVENTION

In order to achieve reliable calibration for acoustic thickness sensing systems, a so-called coupon is provided as a reference source that is attached to the interior of the ship hull and is read by ultrasonic test equipment. The ultrasonic probe used is scanned across the surface of the hull in a raster pattern, with timing of acoustic reflections being used to build a raster scan of the inspection area. The raster scan is first used to locate the coupon, which carries a fiducial element as well as a binary signature to identify which coupon is being read. Note that both the fiducial element and the binary signature are acoustically readable.

Once having found the coupon, located its fiducial point and ascertained its identity, a stepped material thickness calibrator block is scanned, with the thicknesses set to correspond to expected thicknesses of hulls to be surveyed. Reflections from the surface of the hull, the interface between the coupon and the hull, and the stepped surfaces of the calibration block are used to automatically calibrate the system. This is accomplished by multiplying the thickness of the step in the calibration block whose thickness most closely matches that of the hull with a ratio of the time it takes for an acoustic signal to propagate through the hull material divided by the time it takes for an acoustic signal to propagate through the coupon material.

By selecting which of the stepped surfaces most closely corresponds to the expected hull thickness, and by multiplying this thickness by the ratio derived above, one arrives at an accurate hull thickness that is calibrated by the coupon in the exact environment in which the measurement is made.

In one embodiment, the time through the hull and the coupon material are measured in terms of the zero crossings of the waveforms constituting the reflected waves from the surface of the hull, the interface between hull and coupon and the selected step of the calibration block. Thus, the system is not amplitude dependent, making the accuracies achievable below one-half of one percent of the hull thickness.

In short, thickness measurement accuracies of less than one thousandth of an inch are routine using the subject system that offers in situ calibration.

The position and identity of the coupon are established by providing the coupon with an acoustically readable fiducial element and an acoustically readable binary coding element. The fiducial element includes opposing sectors that intersect at a point to provide a fiducial point for the coupon. The identity of the coupon is provided by bar code elements of differing heights, separated by acoustic isolation material, with the differing heights constituting a binary code readable by the acoustic sensor to determine the identity of the coupon.

How the coupon is attached to the interior of the hull requires that the interface between the interior wall of the hull and the coupon be flat and uncorrupted by acoustic property changing materials. In one embodiment, the interior of the hull is prepared by cleaning, after which a mold is placed over the area at which the coupon is to be mounted. The mold contains cavities into which the various elements of the coupon are inserted. The coupon contains as elements the calibrator block, the fiducial sector block, and the binary coding bar code, as well as piezo-electric transducers for projecting acoustic energy out at two different frequencies to identify to a diver or other instruments, outside the hull, the approximate location of the coupon.

Each of the above elements or devices is located in a separate cavity within the mold and is cemented to the interior wall of the vessel, using anaerobic adhesives.

After the above elements or devices have been adhered to the interior surface of the hull, the mold is removed and a housing, cabinet or compartment is placed over the mounted elements. Thereafter, an acoustic-deadening foam is injected into the housing. This damping material is used to cancel reflections created by acoustic interrogation signals as they pass through the coupon, with the damping material in one embodiment composed of two or more layers of material with a high acoustic impedance differential. Note that the damping material absorbs the acoustic energy during the scan process.

The result is that one can perform in situ calibration of acoustic thickness sensing apparatus by using a calibration block of the same material as the hull, and by providing aids to obtain the location of the coupon, which include piezo-electric transducers for the rough location and a fiducial element for precise location of the coupon. The coupon is also identified through a binary code represented by two different levels of adjacent bars spaced apart by acoustic insulating material in a bar code arrangement.

In summary, a system is provided for calibrating an acoustic hull integrity sensing system by providing a coupon attached to the interior surface of the hull, in which the coupon has a stepped calibration block, with one of the steps approximating the thickness of the hull to be measured at the position of the coupon. The stepped calibration block is made of a material with the same acoustic properties as that of the hull. Acoustic energy is propagated towards the hull and passes through the hull, the interface between the hull and the block and to the interface between the stepped surface and the surrounding material, with reflected acoustic energy having a time of arrival at a sensor measured through the use of zero crossing detectors, in which the thickness of the stepped block that most closely approximates that of the hull is multiplied by a ratio that is the time for energy to propagate through the hull, divided by the time for the energy to propagate through the stepped block. The coupon is also provided with acoustically readable elements, including a fiducial element to determine the exact location of the coupon, and a binary signature bar code element having alternating bars interspersed with acoustic deadening material to identify the coupon. Moreover, piezo-electric transducers are used as pingers to provide an indication of the approximate location of the coupon from a position outside the hull.

BRIEF DESCRIPTION OF THE DRAWINGS

These and other features of the subject invention will be better understood in connection with a Detailed Description, in conjunction with the Drawings, of which.

DETAILED DESCRIPTION

Figure 1:
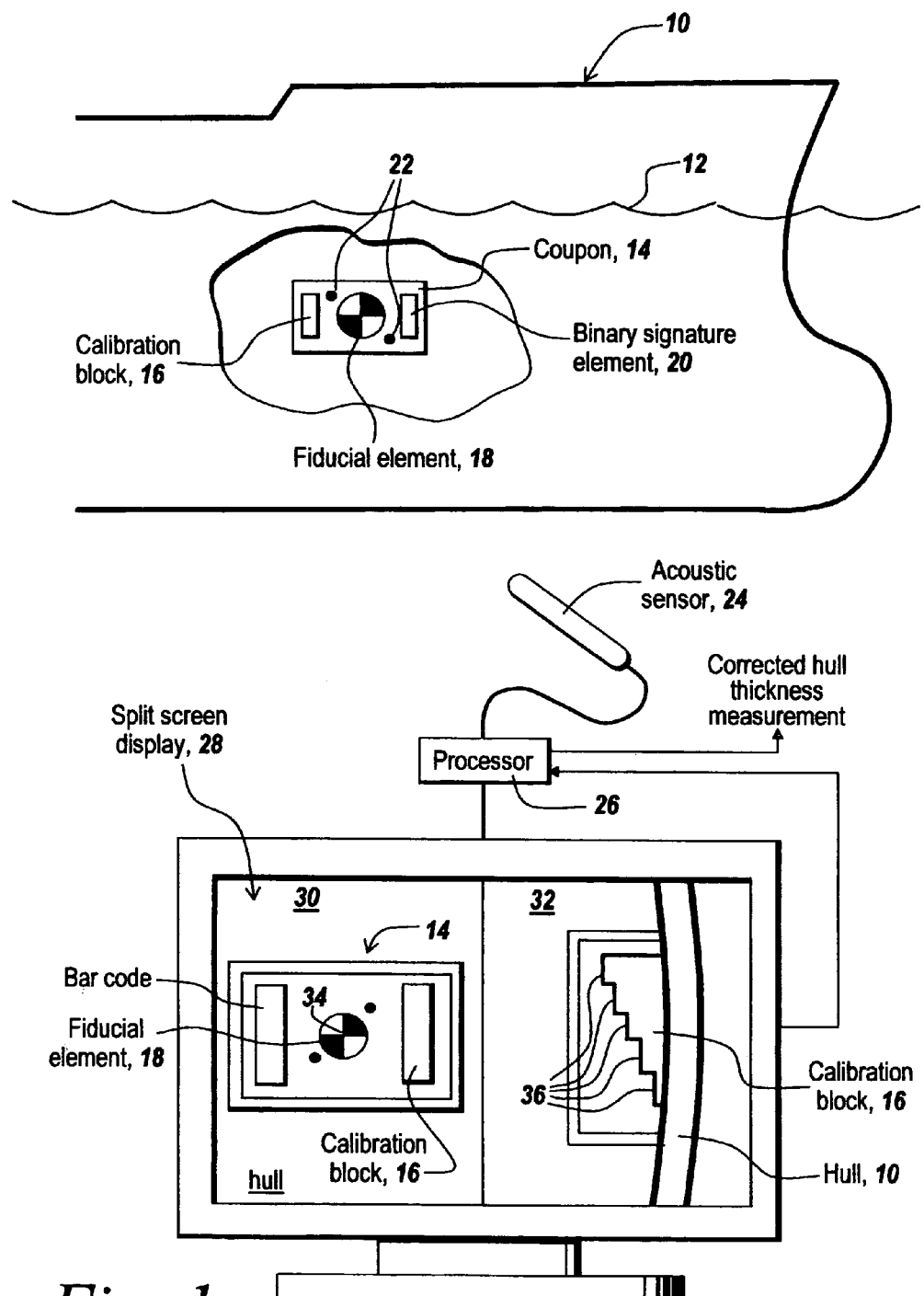
FIG. 1 is a diagrammatic illustration of the placement of the subject coupon at the interior surface of a ship hull in which the coupon carries a calibration block, a fiducial element and a binary signature bar code coupon identification element, with acoustic energy reflected from the coupon detected by an acoustic sensor coupled to a processor, which reconstructs the acoustic image of the hull and coupon and displays this image at a split screen display for displaying a plan view of the coupon from detected returned acoustic energy and the side view thereof to permit comparison between the steps of the calibration block and the thickness of the hull.

Referring now to FIG. 1, a ship's hull 10 floating at the surface 12 of the ocean or body of water, is provided with a coupon 14 at the interior surface of the hull in which the coupon carries a calibration block 16, a fiducial element 18, a binary signature bar code coupon identification element 20 and piezo-electric transducers 22.

As will be described herein, calibration block 16, fiducial element 18, and binary signature bar code identification element 20 have surfaces that are cemented and acoustically coupled to the hull so that when acoustic energy is projected through the hull, the energy reflected from these elements can be read out in terms of the position thereof.

In order to do so, an acoustic sensor 24 is raster scanned in the vicinity of the coupon at the outside surface of the hull, with the output thereof provided to a processor 26, which in turn drives a split screen display 28. The split screen display has two regions 30 and 32, with region 30 projecting the reconstructed image of coupon 14 in plan view. The purpose of this image is to be able to locate the center 34 of the fiducial element 18 so that the precise location of the fiducial point can be ascertained relative to the position of the acoustic sensor.

Screen portion 32 is a side view of calibration block 16, which shows calibration block 16 adjacent hull 10 so that a visual comparison can be made between the step heights 36 so that one can determine by whatever means which of the step heights has a thickness which most closely corresponds to the reconstructed image of the hull.

In operation, the coupon is used as a reference source that is read by ultrasonic test equipment. The ultrasonic probe or sensor described above is scanned across the hull surface in a raster pattern. The output data, timing of acoustic reflections, is used to build a raster scan of the inspection area on display 28, which is then used to locate fiducial element 18 and read the binary signature provided by binary signature bar code coupon identification element 20. The timing data from the scanning of the material thickness calibrator block 16 is used to calibrate the ultrasonic measurement system for subsequent thickness measurements.

The coupon system consists of a housing lined with acoustic dampening material, the two piezo-acoustic devices 22, material thickness calibration block 16, fixed reference point fiducial element 18, binary signature bar code coupon identification element 20, urethane epoxy and a hermetically sealed connector that is attached to the dry side of a ship hull or inner tank or can be submersed if the dry side is not accessible.

Figure 2:
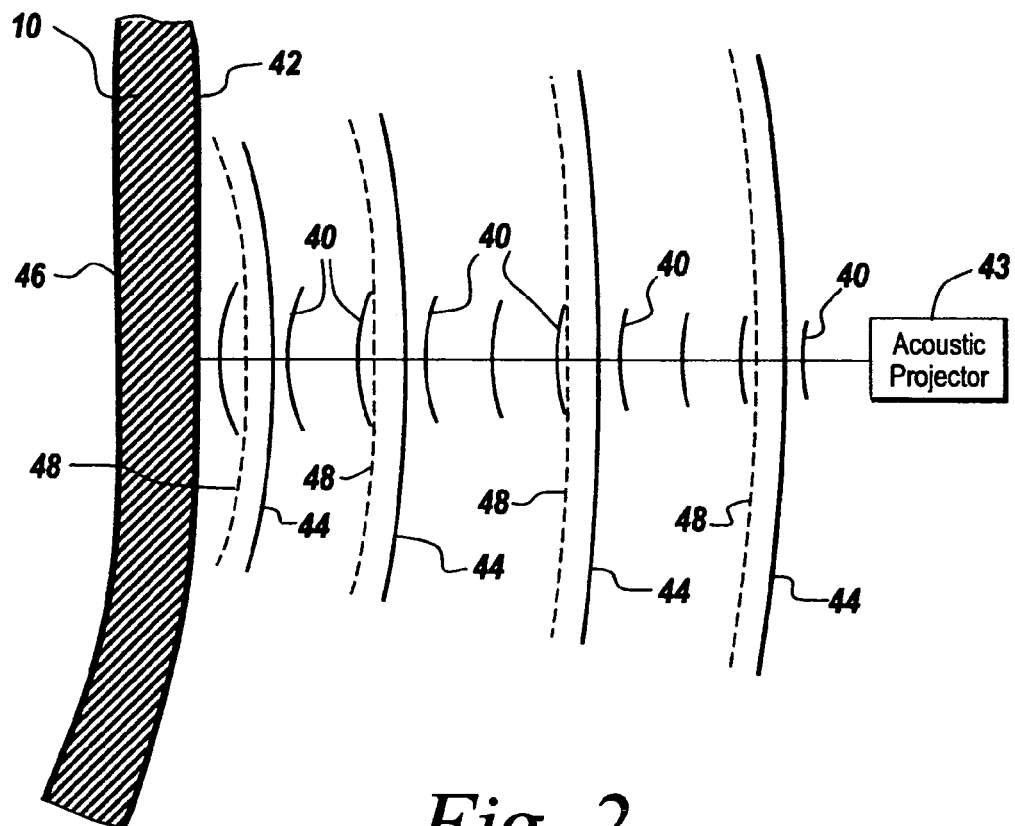
FIG. 2 is a diagrammatic illustration of the projection of acoustic energy towards a hull, with reflected energy from the front surface and the back surface returned in the direction of the acoustic projector.

Referring now to FIG. 2, acoustic energy 40 is projected by a projector 43 towards hull 10 where it is reflected by the surface 42 of hull 10, as illustrated by returned acoustic waves 44.

The back surface 46 of hull 10 produces reflections of acoustic energy 40, here illustrated at 48, which propagate from the back surface as illustrated.

Figure 3:
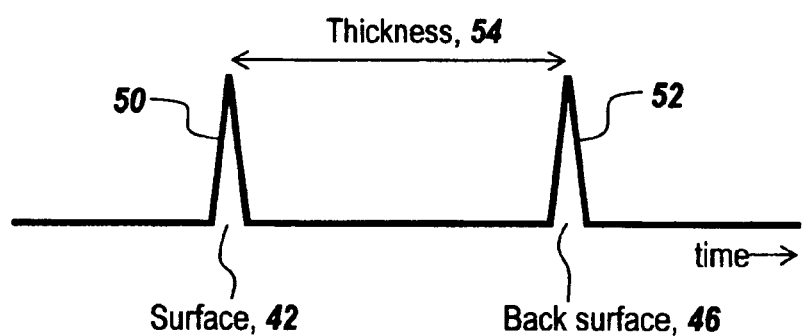
FIG. 3 is a waveform diagram showing that the thickness of the hull of FIG. 2 can be determined by pulses representing the returns from the outer surface of the hull and the back surface of the hull.

Referring to FIG. 3, the timing of the returned pulses at acoustic sensor 24 of FIG. 1 results in a time trace as illustrated by spike 50, which is the first of the returned pulses to be received, followed by a return from the back surface 46 of hull 10 as illustrated by spike 52. It is the time difference between these two spikes that directly measures the thickness of the hull as illustrated by double-ended arrow 54.

Figure 4:
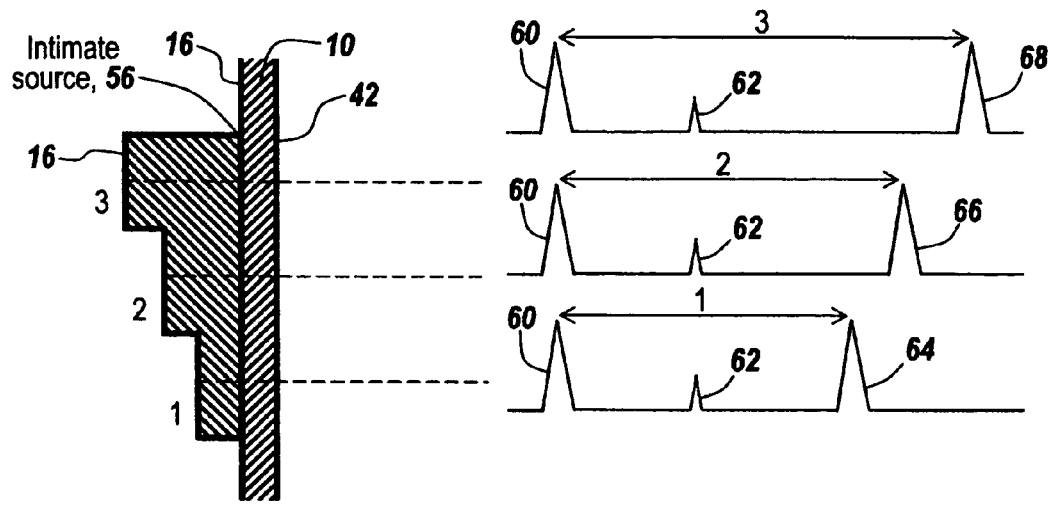
FIG. 4 is a diagrammatic illustration of the use of the subject calibration block in which acoustic energy projected through the hull is returned by the step surfaces of the calibration block so as to provide a time difference between the return from the outer hull surface, the interface, and one of the step surfaces of the calibration block, thus to indicate distance and, correspondingly, thickness.

How to make this measurement more accurate, or at least calibratable, requires in the subject invention, and as illustrated in FIG. 4, the intimate coupling 56 of calibration block 16 to the interior surface 46 of hull 10.

For convenience, the stepped surfaces of block 16 are labeled, 1, 2 and 3 as illustrated. It is noted that block 16 is of a material that is to acoustically match the hull alloy or material.

As can be seen in the waveform diagrams to the right of block 16, the first surface provides a spike 60, which relates to the return from the surface 42 of hull 10. Interface 56 results in a spike 62 as illustrated. Finally, the spikes 64, 66 and 68 refer to the timing of the energy returned from steps 1, 2 and 3 respectively.

Figure 5:
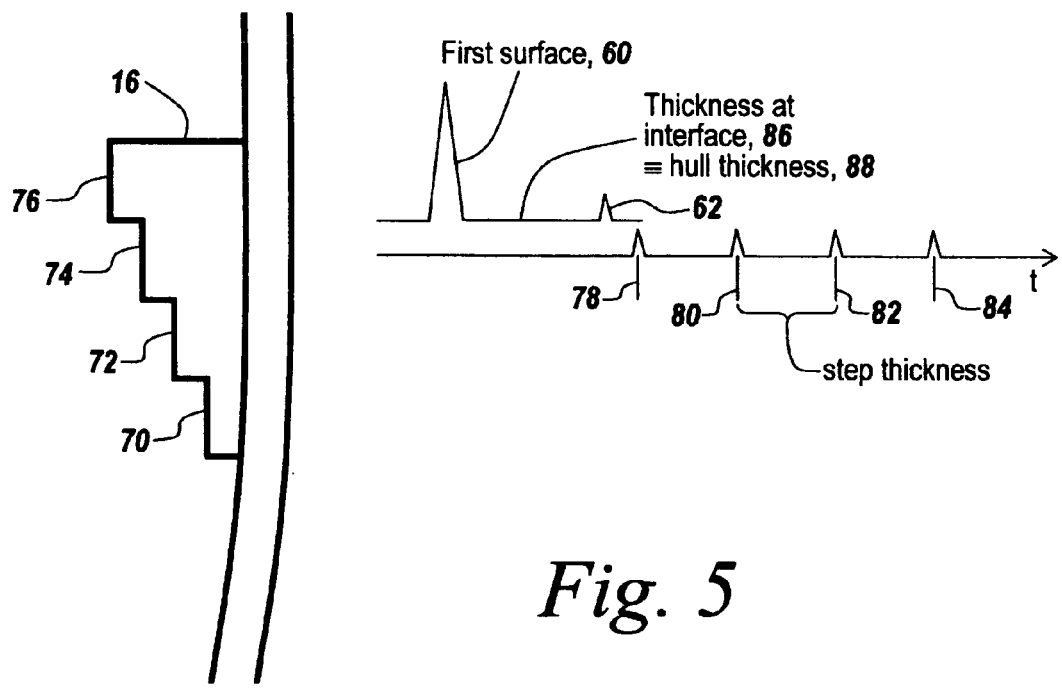
FIG. 5 is a diagrammatic illustration of the position of the returns from the stepped surfaces of the calibration block as compared with returns from the interface between the calibration block and the hull, in which the position of the interface is compared to returns from the stepped surfaces.

Referring to FIG. 5, one way of understanding the calibration offered by calibration block 16 is to understand that the returns from steps 70, 72, 74 and 76 are as illustrated at 78, 80, 82 and 84 respectively. Note that the time difference between spikes 78, 80, 82 and 84 correlate to the step thicknesses of the calibration block. Since the thickness of the calibration block is carefully controlled and is therefore known, if one compares the thickness at the interface as illustrated at 86, as measured against the step thickness measurements 78-84, one can obtain a calibrated hull thickness 88.

Figure 6:
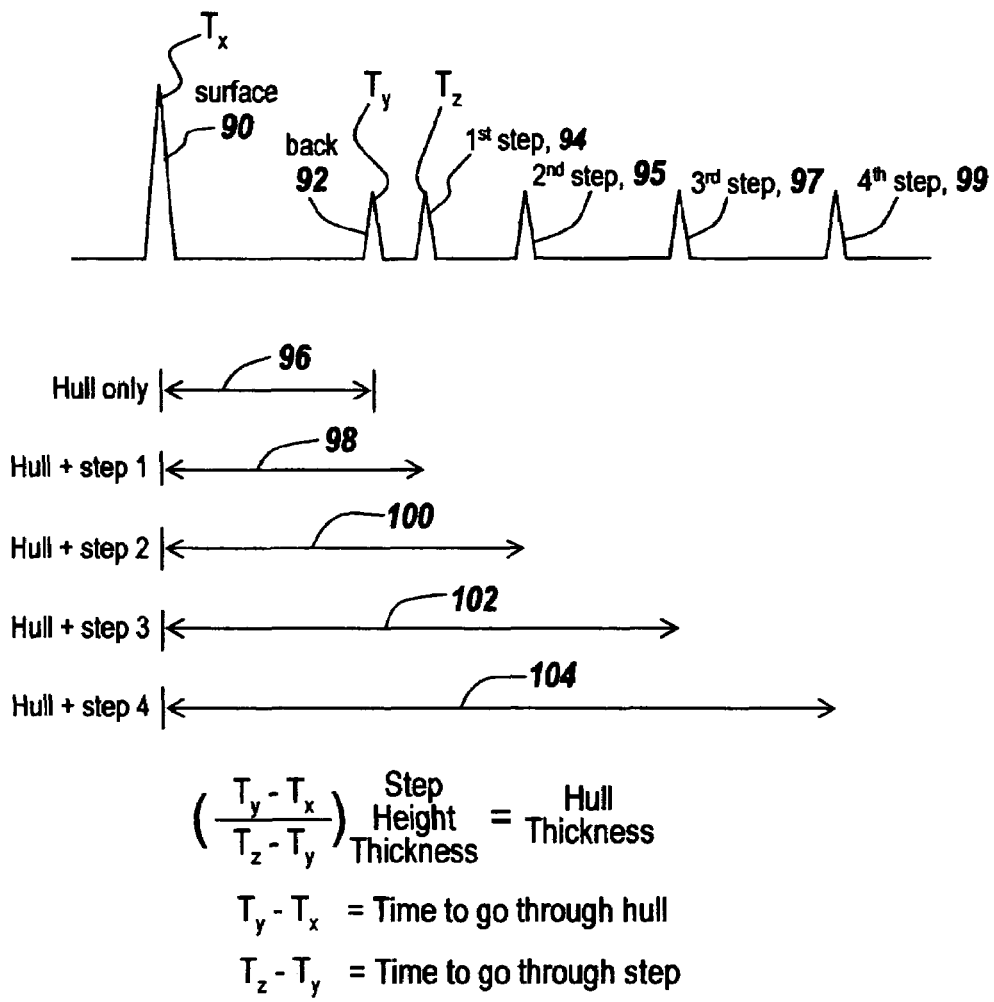
FIG. 6 is a waveform diagram illustrating the time difference and thus the thickness of the hull only, the hull plus Step 1, the hull plus Step 2, the hull plus Step 3, and the hull plus Step 4, thus to derive $T_y-T_x$, the time for acoustic energy to go through the hull, and $T_z-T_y$, which is the time for acoustic energy to go through a step.

Another way of visualizing the operation of the calibration block is to consider more particularly FIG. 6. If the time of arrival of the returned pulse from the surface of hull 10 is illustrated by spike 90 and is designated by $T_x$, and assuming that the spike from the back surface 92 is designated $T_y$, and further noting that the spike 94 from the first step is designated $T_z$, then as can be seen from double-ended arrows 96, 98, 100, 102 and 104, one has time differences corresponding to acoustic energy passing through the hull only, the hull plus Step 1, the hull plus Step 2, the hull plus Step 3, and the hull plus Step 4 respectively.

As can be seen from the equation below these arrows, one can derive a ratio of the thickness of the hull as measured by $T_y-T_x$ to the thickness of the calibration block as measured by $T_z-T_y$. This ratio is to be multiplied by the step height thickness that most closely corresponds to the thickness of the hull as determined by optical inspection or otherwise in accordance with FIG. 1 such that the selected step height thickness is multiplied by a ratio in which the calibrated block is sensed in the denominator to obtain hull thickness.

Using the zero crossing detection technique to be described, it is possible to derive hull thickness accuracies on the order of 0.5% or in most cases providing a thickness measurement accuracy of less than one thousandth of an inch. Such accuracies permit detection of hull wasting, erosion or deterioration in terms of, for instance, the wasting of paint layers, or the erosion of the thickness of the hull due to rusting and the like.

Figure 7:
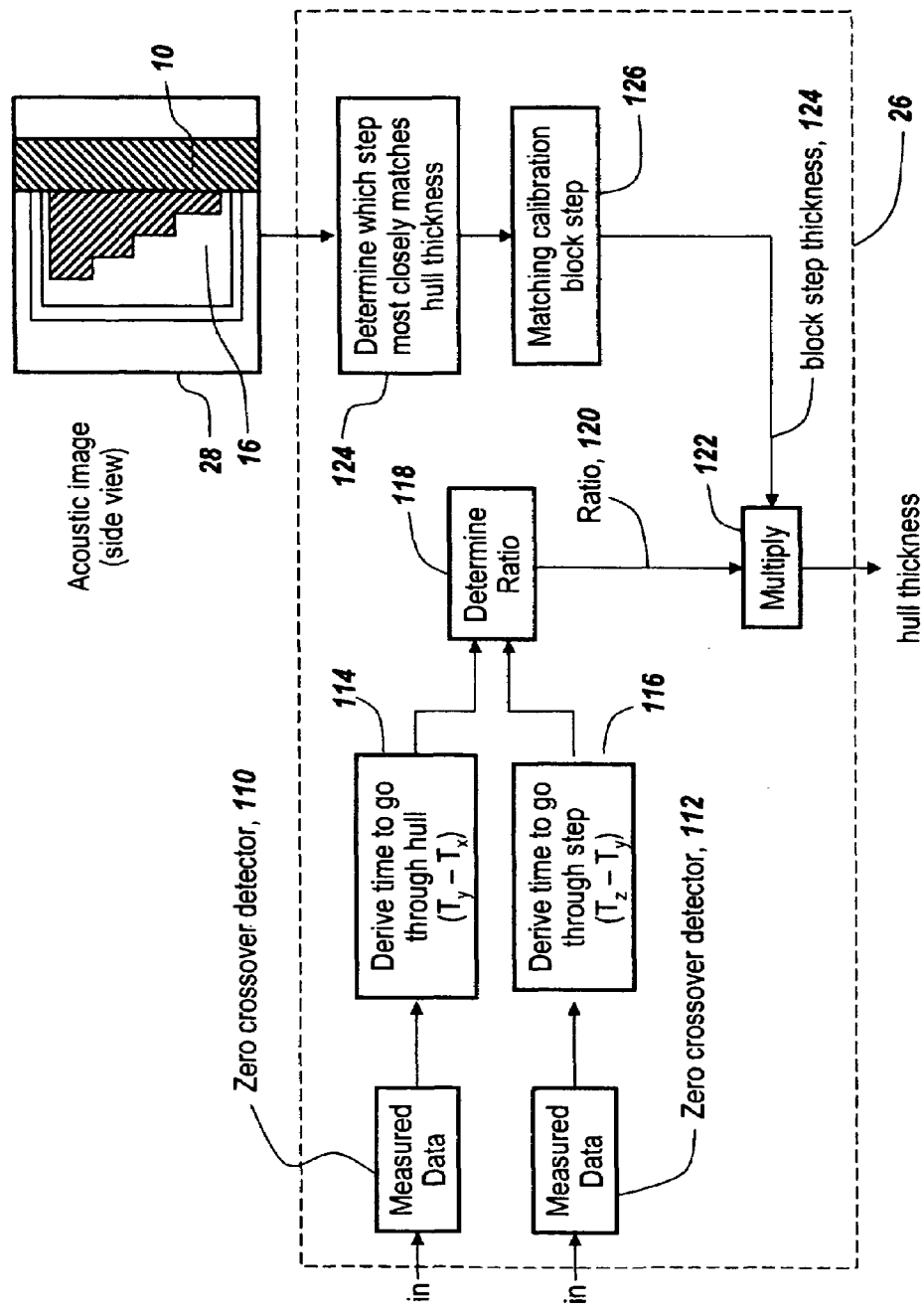
FIG. 7 is a block diagram of the subject calibration system in which the block step thickness corresponding to the thickness of the hull is multiplied by a ratio of the time for energy to go through the hull divided by the time of the energy to go through the step that most closely approximates the thickness of the hull, thus to provide a ±0.5% accuracy.

Referring now to FIG. 7, the output of the acoustic sensor 24 of FIG. 1 is applied to zero crossover detectors 110 and 112, with the output of zero crossing detector 110 reflecting measured data. The first zero crossing of the returned energy is what determines the exact measurement of the time that the return pulse arrives at sensor 24 of FIG. 1. This pulse is used by processor 26 to derive the time for acoustic energy to go through the hull, namely $T_y-T_x$, and to derive the time for the acoustic energy to go through the selected step, namely $T_z-T_y$. The output of the derivation units 114 and 116 is applied to a divide-by circuit 118, which determines the ratio 120, which is to be multiplied at 122 by that calibration block step thickness 124 determined to be the closest to the observed thickness of hull 10. The particular step selected can be made by observation from display 28, which displays the reconstruction of hull 10 and calibration block 16 as illustrated. This manual selection is illustrated at 124 and can be made either by inspection or automatically as desired, with the selection of the matching calibration block step illustrated at 126 being that block step thickness that is to be multiplied by the above-mentioned ratio.

Figure 8:
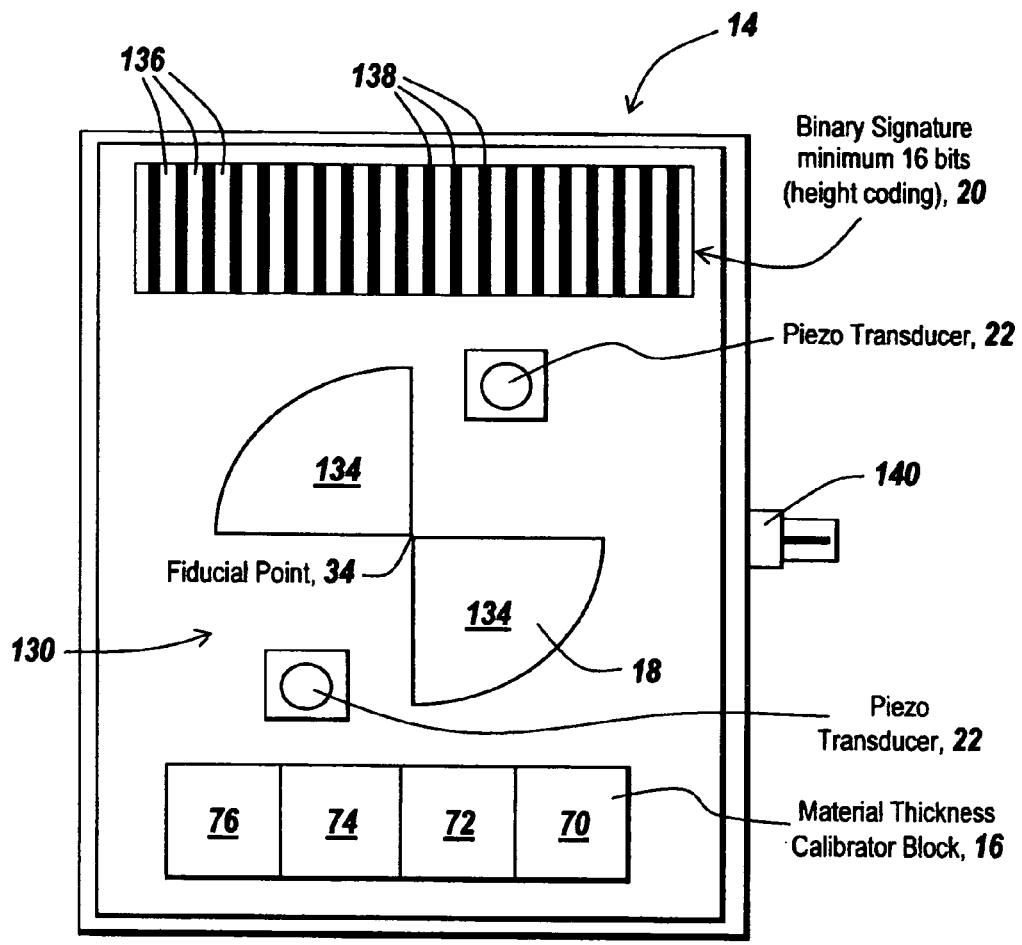
FIG. 8 is a plan view of the subject coupon illustrating the material thickness calibration block, the fiducial point element, the piezo-electric transducers, and the binary signature bar code system.

Referring now to FIG. 8, coupon 14 is shown in plan view in which the stepped material thickness calibrator block 16 is illustrated as being provided with steps 70, 72, 74 and 76.

It is noted that the material thickness calibrator block is a rectangular device made of acoustically similar material as the wall to be scanned, with dimensions of n×4n. The thickness of the device varies over its length at an interval of every n, where n is the device width. The thickness variation is Z, 3Z/4, Z/2 and Z/4 respectively, where the wall to be scanned is between Z/4 and Z in thickness. It is noted that all of these elements are surrounded by acoustic absorbing material 130.

As to the fiducial element 18, two identical metallic 90° sections 132 and 134 of a circle are set at opposite quadrants of an imaginary circle of the same size to create a fiducial point 34. It is noted that the metallic sections are acoustically readable in terms of returns from the surfaces thereof opposite that of the hull.

In order to provide the binary signature for the bar coding element 20, in one embodiment there are a minimum of 16 bits that correspond to a minimum of 16 rectangular metallic bars 136. The dimensions of these bars are n×6n that will either be n or 2n in thickness. The rectangular metallic bars are separated at a distance of n/2 where n is the width of the rectangle and the distance n/2 is filled with acoustic dampening material 138 such that the acoustic dampening material is interspersed between the rectangular metallic bars. The metallic bars are arranged in a defined order to create a binary code where n thickness equals a binary 0 and the 2n thickness equals a binary 1. Note that the binary code is unique for each coupon.

As mentioned hereinbefore, the coupon is provided with piezo-electric transducers 22, which provide acoustic energy when supplied by power from a connector 140. Note that these piezo-electric transducers are positioned in the open area between quadrants 132 and 134 to opposite sides of fiducial point 34.

The housing with the connector and piezo-electric devices mounted and wired has multiple layers of acoustic dampening material 130 attached to the bottom and connector side, taking care to ensure that the connector and wiring are encapsulated. The damping material is used to cancel reflections created by the interrogation signal as it passes through the coupon. The damping material is composed in one embodiment of two or more layers of material with high acoustic impedance differential. The damping material absorbs the acoustic energy during the scan process so that an accurate reconstruction of the coupon can be made.

The piezo-electric elements are driven with discrete high voltage bursts at specific frequencies to allow the positioning system to identify the coupon and home in on its location. The piezo-electric drive system is only activated during the homing phase of the operation, with the piezo-electric transducers being turned off upon achieving a position lock. The piezo-electric drive is a self-contained waveform driver and a high voltage amplifier that may be slaved to an external computer in order to coordinate a number of coupon systems. When used with multiple coupons, each piezo-electric driver set will operate at a discrete combination of frequencies.

As mentioned hereinbefore, the attaching of the coupon is critical to accurate calibration. The attachment of the coupon elements and housing differs slightly depending on the hull or vessel material. The common requirement of the system is that it must be mounted on a non-layered surface and the surface material must have a consistent material density.

The most common application is steel hull or vessel walls. In this application the surface is required to be cleaned of any coatings or corrosion and is lapped to produce a flat surface. The coupon elements for steel applications are machined from alloys matching the steel vessel material to reduce acoustic impedance mismatching.

A template supports the elements during the mounting process to ensure precise alignment. For steel applications, an anaerobic metal ion transfer adhesive is used to produce the thinnest bond possible. This adhesive has a fast bond time, facilitating assembly of the coupon elements. Each element is mounted through the template and is adhered to the surface. An outline of the template is drawn on the surface to ensure proper alignment of the housing. The housing pre-assembly is then mounted to the surface using a fast-curing epoxy. Thereafter, the housing is injected with a urethane compound having acoustic absorbing properties. To ensure that no gas pockets are entrained in the casting, the assembly is evacuated.

The preparation and assembly process is similar for aluminum surfaces, with the exception of the use of matching aluminum alloy for the coupon elements.

Fiberglass, wood and Ferro cement hull or vessels require special surface treatment to ensure good acoustic visibility from the opposite side of the surface. The interior surfaces are cleaned and sanded and lapped to produce a smooth, void-free attachment surface. The hull or vessel material is to have a constant density and is not cored. If not, there may be a requirement to remove the inner hull or vessel layers before mounting. The elements are attached to the mounting template with methyl-acrylate adhesive and are held in place until cured. The coupon housing is installed in the same manner as that associated with steel and aluminum applications, but may require the addition of a procedure where inner surface layers are removed to achieve a clear acoustic pathway to the coupon elements.

More particularly, prior to any measurement process, one applies the coupon to the inner hull. One typically uses a water jetting system coupled tightly to the hull to remove any paint or coatings from the inner hull. The reason that a water jet is used is to avoid any potential of explosion. This is because areas to which the coupons are to be applied vary from being a ballast tank to storage of flammable materials. One needs to have the inner surface to be extremely clean and flat. In some cases, as necessary, one may have to perform a surface grinding step, again in a water environment, on the inside of the hull to produce a smooth, flat surface on which to mount the coupon. After the inner surface has been prepared, one overlays a mold that has cutouts for the stepped calibrator block, the lobes for the fiducial mark, and the bars for the binary code, plus pockets for the piezo-electric transducers. The mold is temporarily adhered to the hull and anaerobic adhesives which are less than one molecule thick are used to adhere the material, whether it be steel on a steel hull, aluminum on an aluminum hull, or aluminum on a glass or composite hull.

The assembly thus formed is held in compression against the hull until the adhesives have had an appropriate time to set. Thereafter, the mold is removed and a housing is clamped on over the assembly and filled with a special urethane-silicon compound that has the characteristics of absorbing any acoustic energy. The material also physically attaches to the outer housing and the wires and connectors so that it becomes a permanent part of the hull. Note that for a certain type of steel hulled vessel, the steel alloy of the hull is matched by the elements attached thereto. In the case of an aluminum hull, the aluminum alloy is to be matched, whereas in the case of composites or Ferro cement, one would utilize aluminum calibration blocks, fiducial elements and binary signature bar code elements. Note that the above-mentioned urethane-silicone compound is placed in the coupon housing to absorb any acoustic energy in the pathways that are in between the elements or in the back of the elements so that there will be no acoustic return other than from the elements.

In operation, once the acoustic signals have been projected towards the hull, first what one sees is that there is no discrete backwave. What is seen is a so-called noise floor. When there is a backwave, one observes a sharp rise in the amplitude of the waveform, which indicates that the projected acoustic wave has breached an interface. If one measures the timing between the front end of the pulse representing the reflection of the acoustic signal from the outer surface of the hull being measured and the front end of the pulse representing the reflection of the acoustic signal from the inner surface of the hull being measured, through the use of a calibrated scale produced by the stepped block one obtains a precise measurement of the thickness of the hull as a function of time. One therefore can translate the time into a precise measurement of thickness.

In the subject invention, in one embodiment, one actually takes a look at the wave front in terms of the frequency component and phase shift. This is compared with a precisely generated clock so that one actually looks at the zero crossing and takes a look at the number and spacing of the zero crossings to ensure that one is measuring the appropriate waveform. One then back-translates the wave to the start point or the intercept point to get the precise measurement.

Note that the waveform of the projected acoustic signal is distinct. Acoustic energy reflected by the materials being measured is detected as a lower amplitude copy of the projected pulse. Extraneous noise received by the acoustic sensor can produce a constructive/destructive deformation of the received waveform, particularly in the front and back of the projected pulse. One therefore takes a look at the portion of the return waveform which resembles the projected pulse, and uses the first zero crossing of the waveform as the time marker from which to do the calculations. As pointed out hereinabove, other systems look at the average. The problem with these types of systems is that, if the envelope has a smaller wave front, it shifts the point in time that one is using as a benchmark for the thickness measurement. In other words, one extracts a thickness measurement that has an error because of the integration time, which is proportional to the amplitude of the envelope.

Figure 9:
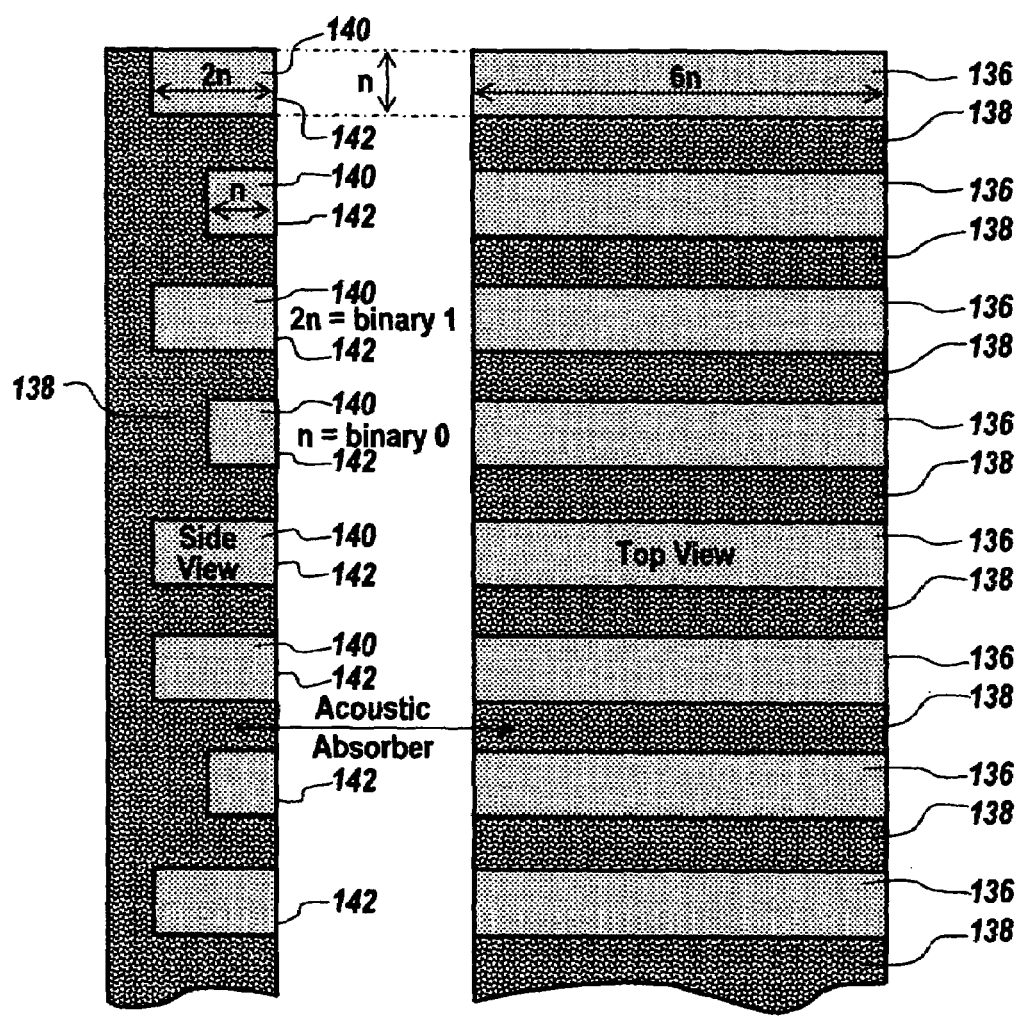
FIG. 9 is a diagrammatic illustration of the acoustically-sensed binary signature bar code element in which a binary code is carried by the height of bars and in which the bars are surrounded by acoustic absorbing material; and, FIG. 10 is a diagrammatic illustration of the ultrasonic transducer probe adjacent the hull at a position where the coupon is located, illustrating the step material thickness calibration block, the sectored fiducial point element, and the binary signature bar code element.

Referring now to FIG. 9, a side and top view of the bar code elements is illustrated. Here, as can be seen, bars 136 are interspersed with acoustic deadening material 138, with the length of the bars being 6n, where n is thickness of the bar.

As can be seen, the binary coding is characterized by bar 136, height 140 being either n or 2n, where n is a binary 0 and 2n is a binary 1. Note that the acoustic absorber material extends over the top of the bars, whereas the bars are intimately coupled to the hull at their interior surfaces 142.

Figure 10:
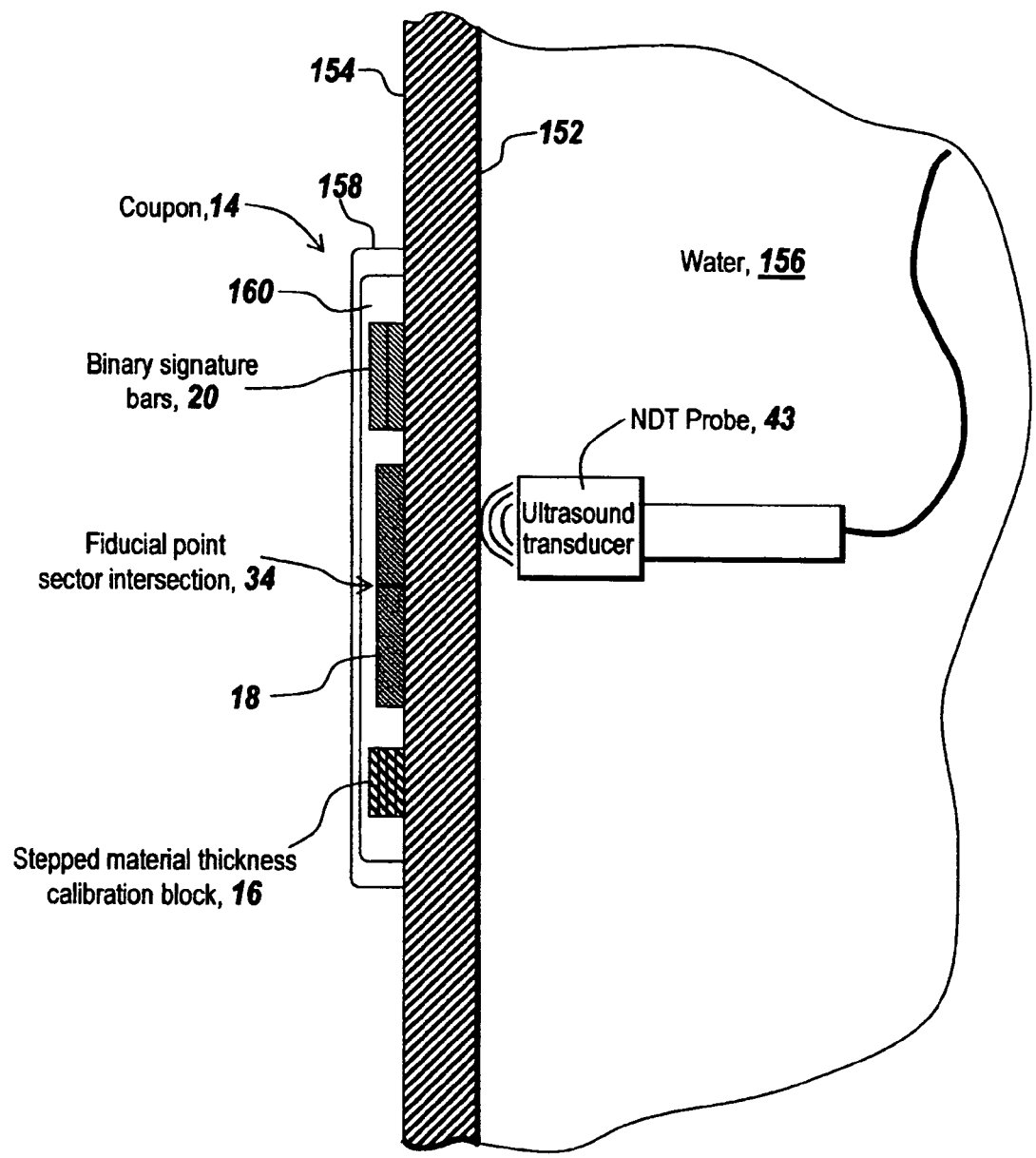

Referring now to FIG. 10, in operation, a non-destructive test probe 43, here in the form of an ultrasonic transducer, is used in the process. Coupon 14 is scanned from the side 152 opposite the mounting surface 154 of the coupon. The non-destructive test probe emits an ultrasound burst that travels through the surface to be measured, through the coupon coupling medium 156, followed by going into the coupon. The coupon elements then return reflections from the ultrasonic burst. The remaining burst energy is heavily attenuated or absorbed in the damping material, further reducing or eliminating return reflections.

The travel time of the acoustic pulse through the hull material and coupon elements is ratiometrically compared to the known thicknesses of the stepped calibration block, yielding the distance. The distance information is then used to determine material thickness.

The entire coupon is scanned in a raster mode, with the probe position controlled by an acoustic positioning system such as described by Greelish in patent application Ser. No. 10/935,986. The initial positioning of the scanning probe is accomplished by homing in on the piezo-electric transducers, which are alternately driven by discrete frequency bursts. The acoustic positioning system triangulates the coupon's acoustic bursts and positions the probe to overscan the coupon location. Subsequent processing locates the fiducial element, interprets the binary signature and calibrates the ultrasound probe for correct material thickness measurement.

Here it can be seen that the step material thickness calibration block 16, the fiducial element 18 having a fiducial sector intersection point 34 and the binary signature bar code bars 20 are in intimate contact with interior surface 134, which serves as the aforementioned interface.

As can be seen, coupon housing 158 is filled with the aforementioned foam 160 so that the measurements garnered by the scan relate only to reflections back through the hull from the surfaces of the calibration block, the fiducial element 18 and the binary signature bars of element 20.

While the present invention has been described in connection with the preferred embodiments of the various figures, it is to be understood that other similar embodiments may be used or modifications or additions may be made to the described embodiment for performing the same function of the present invention without deviating therefrom. Therefore, the present invention should not be limited to any single embodiment, but rather construed in breadth and scope in accordance with the recitation of the appended claims.

What is claimed is:

1. A method for calibrating hull thickness measurements in acoustic hull testing, comprising the steps of:
   locating a stepped calibration block on an interior surface of the hull, the calibrator block having a stepped surface an exact step height from the bottom thereof and being of material acoustically similar to that of the hull;
   projecting acoustic energy towards the hull from outside the hull; and,
   from returns from the surface of the hull, the interface between the block and the hull and the stepped surface of the block calculating the precise thickness of the hull using ratiometric calibration.

2. The method of claim 1, wherein the ratiometric calibration step includes the steps of multiplying the exact step height of the step by the ratio of the time it takes an acoustic pulse to go through the hull divided by the time it takes an acoustic pulse to go through the calibration block at the step.

3. The method of claim 2, wherein $T_x$ is the time that the acoustic pulse is returned from the outer surface of the hull, $T_y$ is the time that the acoustic pulse is returned from the interface and $T_z$ is the time that the acoustic pulse is returned from the surface of the step and wherein the calibrated hull thickness $T=((T_y-T_x)/(T_z-T_y)) \times$ step height.

4. The method of claim 2, wherein the stepped calibration block includes a number of different height steps and wherein the exact step height multiplied by the ratio is that step height most closely approximating the thickness of the hull.

5. The method of claim 1, wherein the acoustic energy projected is pulsed resulting in pulsed returns and wherein the pulsed returns are measured in terms of zero crossings.

6. The method of claim 1, wherein the stepped calibration block is surrounded on all sides but the interface with acoustic absorbing material.

7. The method of claim 1, wherein the location step includes the steps of cleaning the interior surface of the hull at which the block is to be located; providing that the cleaned surface be flat; and bonding the bottom of the calibration block to the cleaned inner surface of the hull using an anaerobic adhesive.

8. The method of claim 7, wherein the location step includes locating a template on the interior of the hull at which the block is to be located prior to the bonding of the block; locating the calibration block in the template prior to bonding of the bottom of the block to the flat inner surface of the hull with anaerobic adhesive; mounting a housing about the block after location of the block in the template, and injecting a compound having acoustic absorbing properties into the housing.

9. The method of claim 8, and further including the step of evacuating the housing prior to injecting the compound.

10. The method of claim 7, wherein the hull is metal and wherein the anaerobic adhesive is in the form of a metal ion transfer adhesive.

11. In an acoustic hull thickness measuring system, apparatus for calibrating the measuring system to derive an accurate measurement of the thickness of a portion of a ship hull, comprising:
a coupon adapted to be mounted to the interior of the hull, including a stepped calibration block adapted to be adhered to an internal surface of the hull, said coupon including an acoustically readable fiducial point having a bottom adapted to be adhered to an internal surface of the hull.

12. The apparatus of claim 11 wherein said fiducial point includes two opposed sectors of a circle having opposed points.

13. The apparatus of claim 11, wherein said coupon includes a housing surrounding said calibration block on all sides but that mounted to the interior of said hull and further including acoustic absorbing material in said housing.

14. The apparatus of claim 13, wherein said acoustic absorbing material includes urethane.

15. The apparatus of claim 11, wherein said coupon includes at least one piezo-electric transducer and power leads thereto for sonically indicating the location of said coupon when said at least one piezo-electric transducer is energized.

16. The apparatus of claim 15 wherein said at least one piezo-electric transducer comprises at least two piezo-electric transducers tuned to different frequencies and further including a second piezo-electric transducer in said coupon tuned to a frequency different from that of said first-mentioned transducer.

17. In an acoustic hull thickness measuring system, apparatus for calibrating the measuring system to derive an accurate measurement of the thickness of a portion of a ship hull, comprising:
a coupon adapted to be mounted to the interior of the hull including a stepped calibration block adapted to be adhered to an internal surface of the hull, said coupon including an acoustically readable bar code having bars of heights corresponding to said code, said bars having bottom surfaces adapted to be adhered to an internal surface of said hull and having acoustic absorbing material between said bars.

18. The apparatus of claim 17 wherein the heights of said bars establish a binary code.

* * * * *